United States Patent [19]
Stepaniuk et al.

[11] Patent Number: 6,028,172
[45] Date of Patent: Feb. 22, 2000

[54] REACTOR AND METHOD FOR SOLID PHASE PEPTIDE SYNTHESIS

[75] Inventors: Nicholas Stepaniuk, Chesterfield; Keith Tomazi, Florisant; Michael C. Stapleton, Pevely, all of Mo.

[73] Assignee: Mallinckrodt Inc., St. Louis, Mo.

[21] Appl. No.: 09/155,798

[22] PCT Filed: Feb. 10, 1998

[86] PCT No.: PCT/US98/02634

§ 371 Date: Mar. 9, 1999

§ 102(e) Date: Mar. 9, 1999

[87] PCT Pub. No.: WO98/34633

PCT Pub. Date: Aug. 13, 1998

Related U.S. Application Data

[60] Provisional application No. 60/037,557, Feb. 11, 1997.

[51] Int. Cl.[7] .............................. A61K 38/00; B01L 3/00; B01J 19/00
[52] U.S. Cl. ....................... 530/334; 530/333; 530/337; 530/338; 422/99; 422/103; 422/129; 422/238; 422/239
[58] Field of Search ..................................... 530/334, 333, 530/337, 338; 422/99, 103, 129, 238, 239

[56] References Cited

U.S. PATENT DOCUMENTS 4,192,798  3/1980  Verlander et al. .................. 530/334
5,186,824  2/1993  Anderson et al. .................. 210/198.2

FOREIGN PATENT DOCUMENTS 0386238   7/1988  European Pat. Off. .
WO90/00932 7/1988  WIPO .

*Primary Examiner*—Michael P. Woodward
*Assistant Examiner*—Abdel A. Mohamed
*Attorney, Agent, or Firm*—Rothwell, Figg, Ernst & Kurz, p.c.

[57] ABSTRACT

A solid phase peptide synthesis reactor system and method of operating the reactor are provided. The reactor system includes a basket rotatable about an axis within a housing and a receiver which delivers fluid to, and collects fluid from, the housing. The basket has a perforate side wall against which a resin cake for the peptide synthesis is formed. The reactor and receiver form a loop or circuit through which solutions are circulated. The circulation of the solutions prevents the reactor from flooding so that the basket will not be submerged in solution and allows for the use of less liquid. Thus greater amino acid concentrations may be used. The method includes forming a resin cake of uniform depth on the wall of the spinning basket and spraying the solutions against the resin cake while spinning the basket. The solutions will pass through the resin cake and drain to the receiver to be circulated or recycled through the system or discharged from the system. Before a subsequent solution is introduced into the reactor system, the prior solution is purged from the system to help control exposure time of the peptide to the solutions.

27 Claims, 5 Drawing Sheets

REACTOR AND METHOD FOR SOLID PHASE PEPTIDE SYNTHESIS

This application claims benefit of Provisional Application No. 60/037,557 filed Feb. 11, 1997.

TECHNICAL FIELD

This invention relates to solid phase peptide synthesis and, in particular, to a reactor system and method utilizing a novel solid phase reactor system in which solid phase peptide synthesis can be carried out on a large scale with increased outputs and yields over those currently available.

BACKGROUND ART

The broader applicability of our system and method to other liquid-solid reactions involving stepwise synthesis on solid substrates, such as the production of oligonucleotides, oligodeoxynucleotides, oligoribonucleotides, oligosaccharides, proteins, etc., will be apparent to those skilled in the art.

Solid phase peptide synthesis (SPPS) was developed by Merrifield in 1963. The basic procedure is well known. The SPPS method typically begins with a polymer gel, such as a partially chlorinated polystyrene cross-linked with divinyl benzene. The C-terminal of a protected amino acid is initially bound to the resin, for example, by means of a benzyl ester of the amino acid. Other binding agents may of course be used. The peptide is synthesized in sequence from the C-terminus with protected amino acids. The amino groups and all reactive side-chain functional groups of the amino acids must be protected by stable blocking groups in order to prevent undesirable side reactions. The blocking groups are selected such that the amino group may be deprotected without disturbing the side chain protecting groups or the link between the C-terminus and the resin. The amino group may be protected by, for example, boc (t-butoxy carbonyl) or fmoc (9-fluorenyl methoxy carbonyl) groups.

The peptide synthesis is typically conducted by the following procedure: The N-terminus of the resin-bound peptide (protected by boc) is deblocked in a solution of trifluoroacetic acid (TFA) in dichloromethane (DCM), for example. The next amino acid in the sequence is coupled to the resin-bound peptide with a coupling agent such as dicyclohexylcarbodiimide (DCC) in a solution of DCM and dimethyl formamide (DMF), for example. An activating agent such as 1-hydroxybenzotrazole (HOBt) may be used to improve the rate and selectivity of the coupling reaction and to decrease racemization. The unreacted amino acid, reagents, and by-products are removed from the resin by washing and filtration. The washing and filtration process is then repeated. The N-terminus of the peptide is then de-blocked, another peptide is added to the chain, the system is then washed and filtered, etc. The process is repeated until all the desired amino acids have been added to the peptide chain in the desired order. The remaining blocking groups are then removed from the peptide, the peptide is cleaved from the resin, and the peptide is collected.

SPPS originally was performed, and often still is performed, in shaken or stirred flasks in which the resin is dispersed. To suspend and mix the resin in a fluid phase, several times the amount of liquid which the resin will absorb or hold is required for the system. Thus, if the resin will hold 10 ml of liquid, 50–100 ml of liquid will be required to disperse and suspend the resin. The increased amount of liquid leads to the use of dilute solutions (typically a 150 mmol amino acid/liter of solution) to minimize costs, since the amino acids are expensive. With dilute solutions, it is difficult to obtain high concentrations of amino acids and hence fast chemical reactions between the amino acids and the growing chain. Further, when the resin is washed and filtered (in a flask) via batch dilution, it is virtually impossible, in a limited number of batch washes, to remove from the resin all the DCM and TFA used. As a result, the contact time of the peptide chain with the DCM and TFA cannot be accurately controlled.

A number of design issues in the reactor development are unique to peptide synthesis. The resin used in solid-phase peptide synthesis is usually a gel resin with a low degree of cross-linking. These resins swell in certain solvents (such as DCM), and shrink in other solvents (such as methanol). The resin volume tends also to increase with the growth of the peptide chain length. In addition, these resins tend to be fairly soft in nature and, thus, are sensitive to physical attrition. A reactor accommodating these characteristics is desired. The amount of exposure time between the peptide-resin and the solvents and reactants used in the synthesis also may be very important. Deprotection of the resin-bound peptide must be complete in order to obtain the highest yield, but the resulting carbocations must not remain in contact with the peptide because of undesirable side-reactions that may occur. Unfortunately, the time required to drain the solution from a resin slurry suspension increases with the depth of the resin bed formed during filtration. Consequently, exposure time of resin-bound peptide to carbocations increases as bed depth increases. As a result, the filtration times for kilogram-scale reactions are far longer than those encountered in bench-scale reactions, so the risk of damage to the peptides due to reactions with carbocations increases with the batch size. Larger scale reactors must therefore be designed in such a way as to mirniize the filtration time. Several solutions to this problem can be selected by the manner of reactor design and through resin particle properties permitted by the reactor design.

In order for a chemical reaction to occur, reactant species must be present at the reaction site within the beads. The reactions involved in the coupling step may be limited by the rate at which reactants (DCC, and the intermediates from the bulk liquid phase of the coupling reactor) permeate through the surface and pores of the resin to internal reaction sites. As is known, the resin, which is typically a polystyrene resin, is effectively formed of porous spheres. The initial amino acid of the peptide chain to be formed is bonded to internal sites throughout the resin matrix. The peptide chain then begins to grow at these sites as the reactant species arrive at the sites.

The rate of mass transfer of reactants from the bulk liquid to the sites within the resin is proportional to the concentration gradient multiplied by the diffusion coefficient of the solute through the solvent (Fick's Law), but it is convenient to think of mass transfer in terms of resistances. Resistance to mass transfer in heterogeneous, solid-liquid processes is evident at two places: (1) across the stagnant liquid film at the surface of the resin particle; and (2) within the pores of the resin particle. Increasing the fluid velocity relative to the resin reduces the film resistance. To reduce resistance to mass transfer within the resin, the resin beads are preferably small and in a gel state (i.e., 5–100$\mu$). The use of more gelatinous resins may permit loadings that exceed 1 mmol of active sites (or peptide chains)/gm resin and approach 2–4 mmol/gm at high yields and conversions. The use of small resin particles is also expected to facilitate better, faster and more complete washing of the resin, because it will be easier to get effective matrix exchange with the wash solvent. Further, the resin beads preferably have a small amount of cross-linking to open up their pores. However, some cross-linking is needed in the resin to give shape and add strength to the resin beads. Resin beads with cross-linking of between 0.2% and 1.0% should be sufficient.

In the synthesis method where amino acids are activated by dicyclohexylcarbodiimide (DCC), the resistance to diffusion into the resin core may be greatly increased by the formation of dicyclohexylurea (DCU), which is essentially insoluble in the solution of 50% DMF in DCM used during the coupling reaction. A shell of insoluble DCU may form on the resin. This deposit of DCU hinders reactants and washes from transferring between the surface and the core of the resin bead. In extreme cases, one may find that diffusion from the bulk liquid phase to the free amines is impossible, and that the only boc-amino acid available for coupling is the material initially present within the resin before the addition of DCC.

The diffusion of reactants into the resin may also be hindered by the formation of the peptide chains themselves. It is generally known that heterogeneous reactions in porous particles typically grow radially inward relative to the outer surface of the particle. It is reasonable to apply this to solid phase synthesis. The bead thus likely comprises a growing shell of reacted peptide and a shrinking unreacted core. If the rate of reaction between the free amine and the activated intermediate is fast relative to the diffusion rate through the resin pores, a shell of reacted peptide, and possibly DCU, will grow radially inward from the surface of the particle. The reaction will take place upon the surface of a shrining core within the resin bead. Reactants must therefore diffuse through an increasingly thick layer of peptide and DCU in order to reach the unreacted core of the resin beads.

One solution to the precipitation of DCU is a change in the chemistry of the reaction system. Resistance to diffusion through DCU-obstructed pores may be reduced or eliminated by forming the symmetric anhydride, o-acyl isourea, and HOBt active ester in a separate reactor (i.e., preactivating the amino acid) and filtering the DCU from the solution prior to introduction into a main reactor where the synthesis is conducted. Similar benefits may be realized if a different coupling agent (such as DIC) is used which does not form an insoluble product during the coupling reaction.

In addition to reducing obstruction by the formation of insoluble compounds such as DCU, pore diffusion limitations also may be reduced by using smaller particles. As a result of decreasing mass transfer resistance, lower concentrations of reactants will be required to obtain the same reaction rate. This may significantly reduce the use of amino acids, HOBt, and DCC required per gram of product.

A numerical analysis of the diffusion to and through the particle is shown in FIGS. 3 and 4. The concentration of reactants will be highest at the surface of the particle and the concentration of reactants within the particle will increase over time as the reactants diffuse or pass into the resin particle. FIGS. 3 and 4 show that the rate of concentration buildup over time ($\tau$) depends on the mass transfer coefficient (H) through the film at the surface of the resin particle and the relative distance zeta =(r/R) through the particle at which the concentration is measured, where R is the overall radius of the particle (particle size) and r is a point measured from the center of the particle. Thus r/R=1 at the surface of the particle and r/R=0 at the center of the particle. Each of the four curves in FIG. 3 represents a concentration profile at a given time $\tau$ when there is no film resistance (H=$\infty$) at the surface of the particle.

FIG. 4 has two plots similar to FIG. 3, but wherein the resistance to mass transfer through the film at the surface of the particle is increased (i.e., H is decreased). By comparing the two plots of FIG. 4 (H=1 and H=3) it can be seen that the concentration within the particle rises more quickly with lower film resistance (i.e., higher H) at the surface of the particle.

FIGS. 3 and 4 show that with significant resistance (both at the surface and in the pores of the particle), the concentration buildup within the particle is slower. This points to a need to reduce both the internal pore resistance and the external surface film resistance so that the mass transfer to the reactants to and through the particle can be increased. Mass transfer of reactants to the resin-bound free amines may be enhanced by increasing the concentration of reactants in the liquid phase, and by decreasing the pore length (using smaller diameter resin particles). In addition, the resistance to mass transfer through the film may be reduced by increasing the velocity of the bulk fluid relative to the resin particles, since film coefficients for spherical bodies are a function of the fluid velocity. A reactor design which addresses these diffusion problems simultaneously is not presently available.

Since the initial development of solid phase peptide synthesis (SPPS) by Merrifield in 1963, a number of innovations have been made in reactor design for peptide synthesis. The earliest reactors were based upon shaken flasks, while later reactor designs included stirred-tank reactors, centrifugal reactors, and tubular reactors. All of these operated with the resin bead suspended or flooded in a liquid phase. Stirred-tank reactors (STR's) are commonly used in peptide synthesis, but they suffer from certain limitations. Because the beads are in suspension, the opportunities to increase the liquid velocity relative to the particles in a stirred-tank reactor are extremely limited. This is because the inertial and viscous forces imposed by the moving liquid upon the suspended particles tend to drag the particles along with the liquid. The fluid velocity field relative to the particles, however, can easily be increased in a packed-bed reactor, in which the resin particles remain fixed, but liquid is forced through the resin bed. However, the bottom frit in both stirred tank and packed bed-reactors required to filter the liquid phase from the resin must be capable of withstanding the pressure differential required for the filtration. As the reactor size is increased, the frit must be fabricated of progressively reinforced materials in order to avoid mechanical failure. On the other hand, if the reactor diameter remains constant, the resin depth on the filter frit increases significantly as the batch size increases. The increased resin depth results in progressively longer drainage and filtration times and exposure times of the resin-bound peptide to the reactants, reactive intermediates, and solvents. For these reasons, neither a stirred-tank reactor with a built-in filter nor a packed bed reactor represent the most efficient type of reactor for a large (multi-kilogram) scale SPPS process.

Although the changes in particle size over the course of the reaction have led to some design difficulties, tubular reactors, such as packed-bed reactors, still offer some advantages over other reactors. Packed bed reactors allow washing to proceed as a displacement operation, rather than a dilution operation as in an STR, provided the amount of "dead volume" between the reactor inlet and the resin bead is minimized. The Reynolds number (Re) in tubular reactors may be very high if the velocity of liquid is high relative to the resin beads. However, high flow rates create high pressures within the reactor, and the high pressures may have a detrimental effect upon the resin. Nevertheless, since mass transfer coefficients increase with increased Reynolds numbers, tubular reactors can have lower liquid film resistance to mass transfer than stirred tank, suspension reactors.

The use of packed beds, however, has its own set of problems. The resin can expand up to 3× its original size when washed with DCM and can shrink to ⅓ its original size when washed with methanol. This can amount to a 9× change in the overall volume of the resin bed. Elimination or minimization of dead volume therefore is very difficult to accomplish. The packed bed, which has a height much greater than its diameter, has a significant amount of wall surface area which impedes the expansion and contraction of the resin bed. When the resin bed is expanded, it packs against the walls of the vessel and reduces the void space between the resin particles. A high pressure thus is required to push all the wash through the bed in the required amount of time. This high pressure can damage the resin beads, create fine particles which may block the filter, and potentially damage or break the filter frit. If high pressure is not used, then flow through the bed will be too slow and the peptides may be allowed to react for too long and may undergo side reactions. Some amino acids or peptide coupling steps are very sensitive to reaction time. Arginine, for example, may react with itself to form cyclic structures instead of coupling to the peptide chain. Exposure time can therefore become a very important factor.

Several attempts have been made to design a tubular reactor which overcomes the constraints imposed by the resins. These prior attempts include:

(1) Ignoring the problems with resin swelling. Verlunder, et al., U.S. Pat. No. 4,192,798 discloses approaches in which the reactor pressure drop is at least 200 psi, and up to 10,000 psi or more. They claimed quantitative yields, and that reactions which take hours in other reactors were completed in minutes. Difficulties with this type of reactor include degradation of the resin, blockage of the outlet frit, maintaining a uniform axial flow throughout the column upon scale-up, inefficiencies in washing due to dead volume, and the cost of the column and high-pressure pumps. This type of reactor is essentially an industrial-scale HPLC.

(2) Allowing axial expansion of the column. Baru, et al., WO 88/909010.6, SU 4117080 developed a zero dead volume reactor in which one end of the reactor was allowed to float with the resin. A small weight was added to the top piston of the reactor to provide a constant force to the floating head of the reactor. As a result, the column was operated at a low pressure drop to avoid spilling solvent out around the top head, making it very sensitive to blockage in the outlet frit. Accumulation of DCU in the bed or within the frit which may increase the pressure drop and could have safety and environmental consequences. In addition, the low pressure drop constraint requires a low liquid velocity, resulting in low Reynolds numbers and possible maldistribution of the liquid flow. The low liquid rates also result in longer exposure times to the reactants and washes.

(3) Use of gel supported by a rigid polymer. Atherton, et al., JCS Chemical Communications, p. 1151 [1981], developed a rigid polymer in which gel could be contained within the macropores. The gel could swell and shrink, but the volume of the rigid polymer beads would remain constant. As a result, high liquid flow rates, low pressure drops, and constant resin volume could be obtained. However, it is most likely that a reduction of mass transfer will occur with these types of supported resins, since the dffusional path of the reactants would increase after adding film and pore diffusion through the supports. In addition, these types of resins are expensive.

(4) Allowance for dead volume. Lapluye and Poisson, PCT publication no. WO 92/115867 developed a piston-type reactor with fritted ends. In this type of reactor, resin is placed in a hollow piston which is cycled upwards and downwards within a larger cylinder full of solvent and reactants. This type of reactor is essentially similar to a shaker or fluidized bed reactor, and the mixing motion of the piston reactor should compensate for the differences in densities of the resin and the solvents. It appears that the efficiency of the washing should be the same as, or somewhat better than, smaller fluid phase volumes than that in an STR. However, the volume of solvent used relative to the resin mass is probably considerably greater than that required by a typical tubular reactor. The Reynolds numbers are probably quite low, and it may be difficult to scale up the mechanics. In addition, heat can be generated due to "viscous dissipation" effects caused by the motion of the piston through the liquid, requiring some additional means of cooling.

At this point, there does not appear to be a tubular reactor which does not have some serious limitations in cost, safety, or efficiency.

Reactors based upon the design of a rotating bowl have also been developed. Rotating bowls or centrifugal reactors can allow for increasing the liquid velocity relative to the resin particle. Birr, German Patent No. 2,017,351, discloses a "washing machine" reactor in which a porous basket is initially loaded with resin, then spun to a moderate speed while submerged in a liquid. The centrifugal forces cause the resin particles to form a bed on the inside walls of the basket, and cause a moderate degree of fluid recirculation through the resin bed. The bowl is flooded (i.e. filled with liquid), as is the resin bed. The drag imposed upon the basket by the liquid bath imposes high torque upon the drive motor, and will also cause the generation of heat. For these reasons, the rotational speed of the Birr reactor will be relatively slow and the relative fluid to solid velocity will be limited. The limits on rotational speed will almost certainly result in a non-uniform resin bed that is shallow at the top and deep near the bottom. The recirculating liquid will tend to follow the path of least resistance, and thus will "short-circuit" through the shallower part of the bed. As a result, the contact between the reactant rich liquid and resin will not be consistent throughout the reactor. In addition, the lower velocity of the liquid with respect to the resin will result in lower mass transfer through the surface film surrounding the particle. Finally, the volume of solvent required to submerge the rotating basket will be large compared to the volume needed to soak the resin charge. This will thus also require a significant volume of reactants relative to the resin mass. This large volume will result in the use of a low concentration solution, which consequently results in a slower reaction rate and longer reaction time. It may therefore require a larger amount of amino acid to maintain the amino acid concentration at a level which will result in acceptable reaction rates.

Another type of centrifugal reactor based upon a flooded "hollow rotor" was developed by Anderson and Anderson, U.S. Pat. No. 5,186,824. The liquid flow path in the Anderson et al. reactor is axial rather than radial, and the geometry is irregular for the liquid flow fields. The point at which liquid is introduced depends upon the density of the liquid in relation to the density of the most recently added liquid. Also, little room is provided for expansion of the resin. As a result of expansion and contraction, the exposure of resin to the liquid phase is likely to be non-uniform. Complete and uniform contact and removal of liquid from the rotor may be very difficult to accomplish.

DISCLOSURE OF INVENTION

One object of the present invention is to provide a method for conducting SPPS which will produce higher outputs and higher yields than that currently available.

Another object is to provide such a method in which the contact time of the peptide chain with the various agents can be more accurately controlled.

Another object is to provide such a method in which the reaction rate is increased.

Another object is to provide such a method which will permit the use of higher concentrations of amino acid than is currently possible without increasing the amount of amino acid used (and possibly using higher concentrations with a smaller amount of amino acids).

Another object is to provide a reactor for such a method.

Another object is to provide such a reactor in which the mass transfer of the liquid through the solid phase is increased.

Another object is to provide such a reactor which will not impede the swelling and shrinking of the resin, and which will not cause resin attrition.

Another object is to provide such a reactor in which the resin bed is substantially uniform in thickness so that fluid flow through the resin bed is uniform.

Another object is to provide such a reactor system which can reduce solvent waste.

Another object is to provide such a reactor which has the ability to "squeeze" solvent from the resin by centrifigal force, thereby eliminating a step of chemically shrinking the resin particles with alcohol, since chemically shrinking the resin may cause aggregation of the growing peptide and may damage the resin.

Another object is to permit a broader selection of resins having different particle size and cross-linking properties that are advantageous to the formation of peptides.

These and other objects will become apparent to those skilled in the art in light of the following drawings and accompanying disclosure.

In accordance with the invention, generally stated, we have provided a reactor system and a method for operating the system which achieves the above noted objectives. The reactor system includes a reactor having a housing and a rotatable basket mounted within the housing. The basket has a perforated, porous, or foraminous side wall upon which a resin cake is formed during a synthesis procedure. A filter cloth or screen is situated on the inner surface of the basket wall and the cake is formed against the filter cloth. The system also includes a solution supply tank or receiver/sump which receives solutions to be introduced into the reactor. The solution supply tank includes an inlet and an outlet. The solution supply tank and the reactor are interconnected to define a loop or circuit through which solution is cycled. The reactor system is operated so that the reactor basket is not submerged in the solution. Thus, the reactor is never flooded with solution and all the solution passes through the resin cake.

The system includes a purge system having a waste collector and valves in the lines interconnecting the reactor and supply tank. The valves are operated to purge a first solution from the system and direct it to waste prior to the introduction of a second solution. The purge system includes a first valve in the line connecting the supply tank outlet to the reactor inlet and a second valve in the line connecting the reactor outlet and the supply tank inlet. The first valve is operated to direct the first solution to waste after the cycle time of the first solution is complete and before the second solution is introduced into the supply tank. The second valve is operated to direct the cycling solution to waste for a short period of time at the beginning of the cycling of the second solution to prevent any of the first solution which may remain in the bed from entering the supply tank which, at that point, contains the second solution.

Preferably, the reactor system also includes a make-up tank in which solutions are prepared (i.e., amino acid solutions are preactivated, the resin slurry is prepared, etc.). The supply tank is in fluid communication with the reactor and the solution supply tank. A valve is operable to selectively direct the contents of the make-up tank to the solution supply tank and the reactor. The valve from the make-up tank is operated to direct the resin slurry directly to the reactor and to direct amino acid solutions, washes, etc. to the supply tank. A filter is positioned between the make-up tank and the supply tank through which preactivated amino-acid solutions are passed. The filter is provided to filter out insoluble byproducts (such as DCU) of the activation reaction. A filter by-pass line is provided so that washes, deblocking agents, etc. do not have to pass through the filter.

The method of operating the system includes (a) spinning the basket at a desired rotational rate and supplying a slurry of activated resin to the reactor basket to build up a cake of substantially uniform thickness (for example, about 2 cm to about 5 cm thick) on the perforated wall of the basket. The resin preferably contains the first amino acid bound to the resin or is otherwise derivatized. If the first amino acid is not bound to the resin, it is now bound to the resin. (b) Supplying a deprotecting solution to the rotating basket to deprotect the N-terminus of the of the resin-bound peptide. (c) Supplying a washing solution to the rotating basket to wash the deprotecting solution from the cake. And (d) supplying an amino acid solution of the next amino acid to be added to the peptide chain and a coupling solution to the rotating basket to add the next amino acid to the peptide chain. The steps (b)–(d) are repeated until the peptide chain is completed.

The solutions (i.e., the deprotecting solution, the washing solution, the amino acid solution, and the coupling agent solution) are introduced into the rotating basket at a rate such that the supplied solution will not build-up in the housing to a point above the floor of the basket, so that all the solution will not build-up in the housing around the basket. Thus, the basket is in an unflooded state during each stage of a peptide synthesis. The resin used is preferably made of polystyrene beads having a diameter of less than $100\mu$ and are preferably 0.2%–1.5% cross-linked. The small bead size and low percentage of cross-linking within the bead will facilitate mass transfer through the beads, thus allowing the rate of reaction to be as high as possible. Larger resin beads can be used in this system, but will then introduce greater mass transfer resistances.

To enable the basket to operate in the unflooded state, the majority of the solution is maintained in the external sump tank, and the solution is pumped into the reactor to pass through the cake and then returned to the sump tank. The solution is then recycled through the reactor resin bed for a predetermined amount of time. This provides contact for as long as needed.

Between each step (i.e., before the introduction of a next or second solution) the prior or first solution is drained and purged from the system to prevent the first solution from contacting the peptide more than a desired amount of time. The draining step includes, after cycling of the solution is stopped, continuing to spin the basket to ensure that nearly all of the free draining first solution is forced out of the cake by centrifugal action and returned to the supply tank. The purging step involves operating the first valve to direct the solution in the sump tank to recovery or to waste.

A small amount of the first solution may remain in the resin at the beginning of the second cycle. When the second solution is introduced into the system, the second valve is opened to waste for a short period of time at the beginning of the cycling of the second solution. Any of the first solution that was not forced out of the cake will be forced or washed out of the cake by the second solution. Opening the second valve to waste as a purge will remove the remainder of the first solution from the system.

Preferably, the amino acids are preactivated, and the insoluble by-products from the activation step are filtered from the amino acid solution, prior to the amino acid solution being introduced into the system.

BEST MODE FOR CARRYING OUT THE INVENTION

Figure 1:
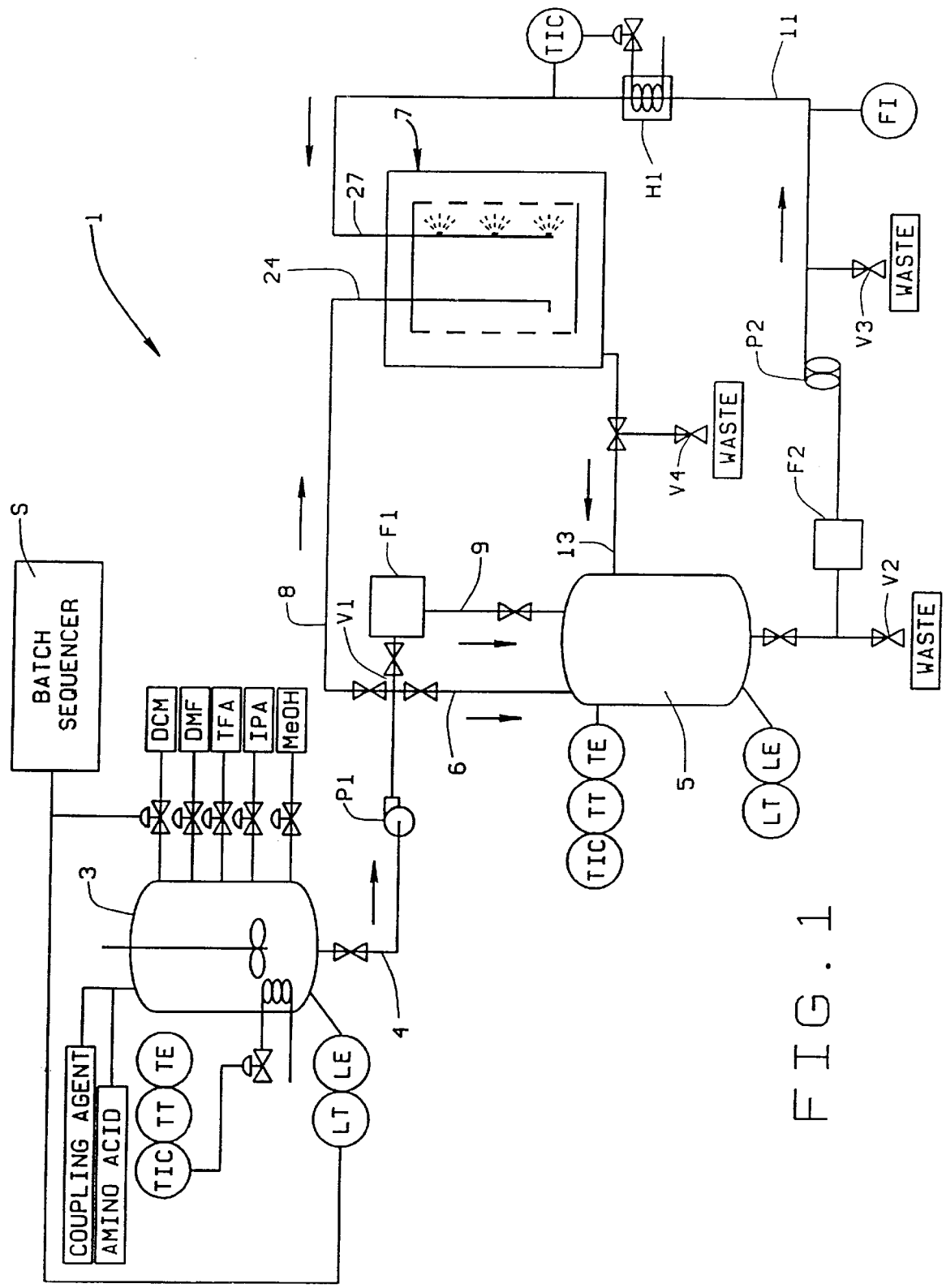
FIG. 1 is a schematic of the equipment set up utilized in the present invention.

An illustrative equipment setup of the present invention is schematically shown in FIG. 1. The system 1 includes a make-up tank 3 provided with an agitator to dissolve the amino acid. A mechanical agitator is preferably used, but other types of agitators could also be used. The solvents and reagents used during the synthesis operations may be charged sequentially to this tank, blended, and optionally adjusted to the desired operating temperature with either internal coils (shown) or an external jacket for heating and cooling. Preferably the make-up tank 3 is also used to preactivate the amino acid. A pump P1 in a line 4 transfers the reactants from the make-up tank 3 to a three-way valve V1 to transfer resin slurry, amino acid solution, or solvents to a receiver/sump 5 over a line 6 or to a reactor 7 over a line 8. If pre-activated amino acids are being transferred to the receiver/sump 5, the amino acids are passed through a filter F1 which is sufficiently fine to remove insoluble by-products, such as DCU, from the pre-activated amino acid solutions. The filtered pre-activated amino acids are then transferred to the sump/receiver 5 over a line 9. As noted above, DCU is a by-product of the activation of the next amino-acid to be added to the chain and can clog the resin beads as well as the system equipment such as spray nozzles and pumps. Passing pre-activated amino-acid solution through the filter F1 to remove the DCU prior to introducing the amino-acid solution into the reactor 7 is thus preferred.

A line 11 leads from an outlet of the receiver/sump 5 to an inlet of the reactor 7. Preferably, the line 11 is provided with a filter F2, a metering pump P2, and a heat exchanger H1. Two valves V2 and V3 are provided on opposite sides of the pump P2 to allow reagents to be directed to "waste" or to "recovery". Preferably, valve V2 is positioned upstream of the filter F2.

Lastly, an outlet of the reactor 7 is connected to an inlet to the sump/receiver over a line 13. A fourth valve V4 is placed in line 13 to direct reagents from the reactor 5 to be directed to "waste" or "recovery".

As can be seen the sump/receiver 5 and reactor 7 are part of a loop defined or completed by lines 11 and 13. The receiver/sump 5 can thus be used to receive discharge from the reactor 7 and maintain an inventory of wash solvents or amino acid solutions for recycling back through the reactor. As will be discussed below, this enables the reactor to be substantially free of pooling liquids.

Figure 2:
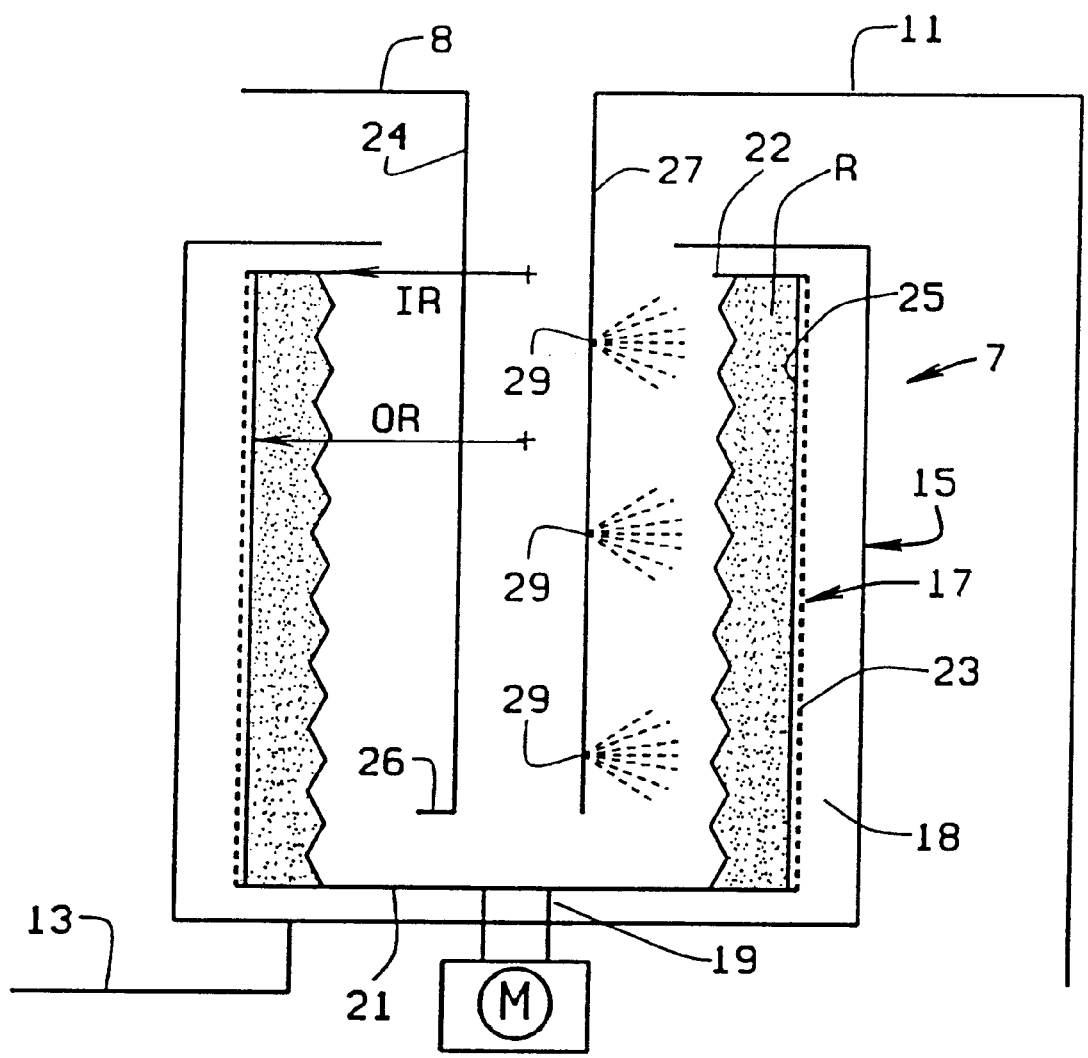
FIG. 2 is an enlarged schematic of a reactor used in the present invention.
Figure 3:
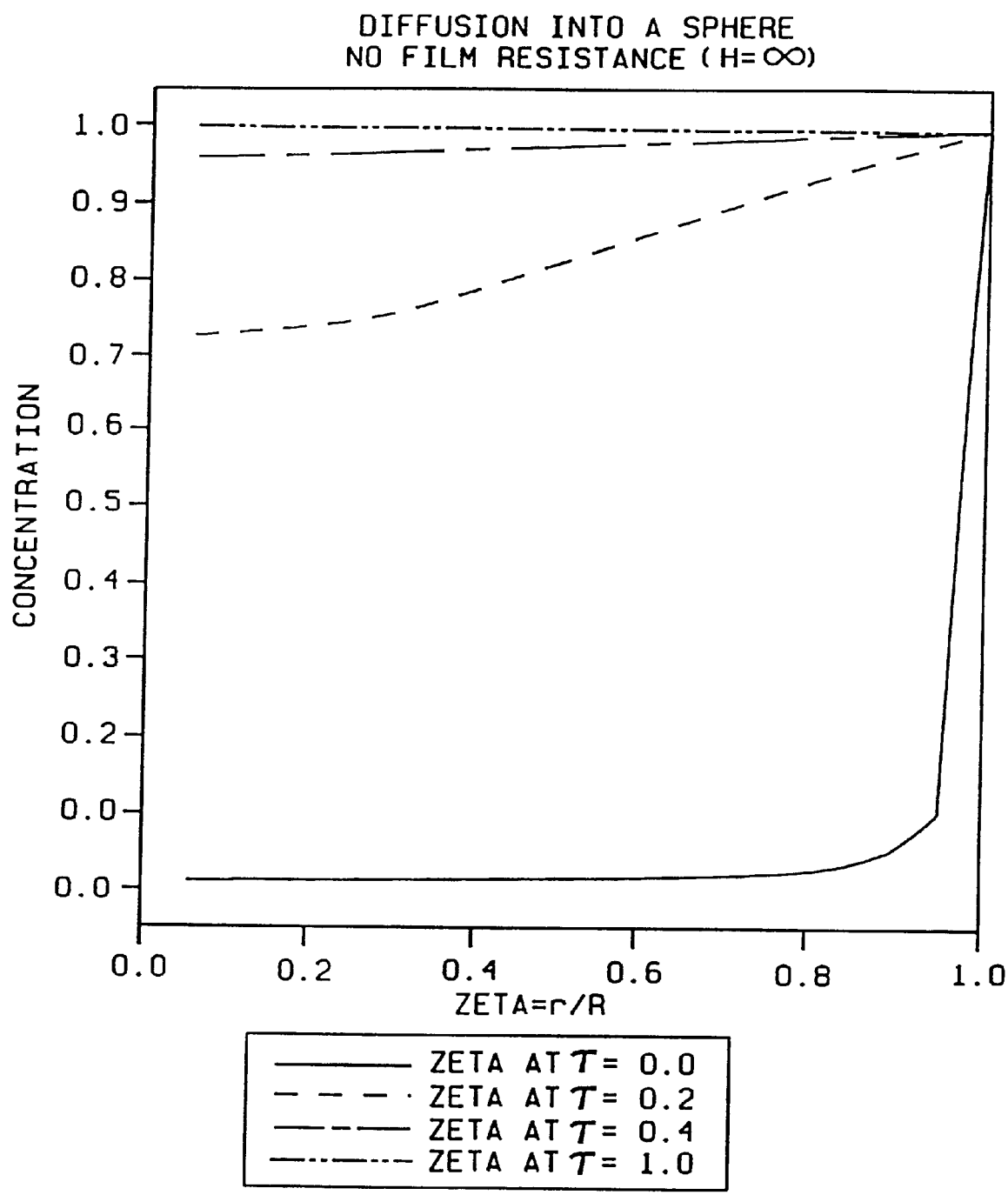
FIG. 3 is a chart showing the concentration of a boc-amino acid as a function of the distance from the center of the particle (denoted by "zeta") at four points in time for no resistant to mass transfer in the liquid film.
Figure 4:
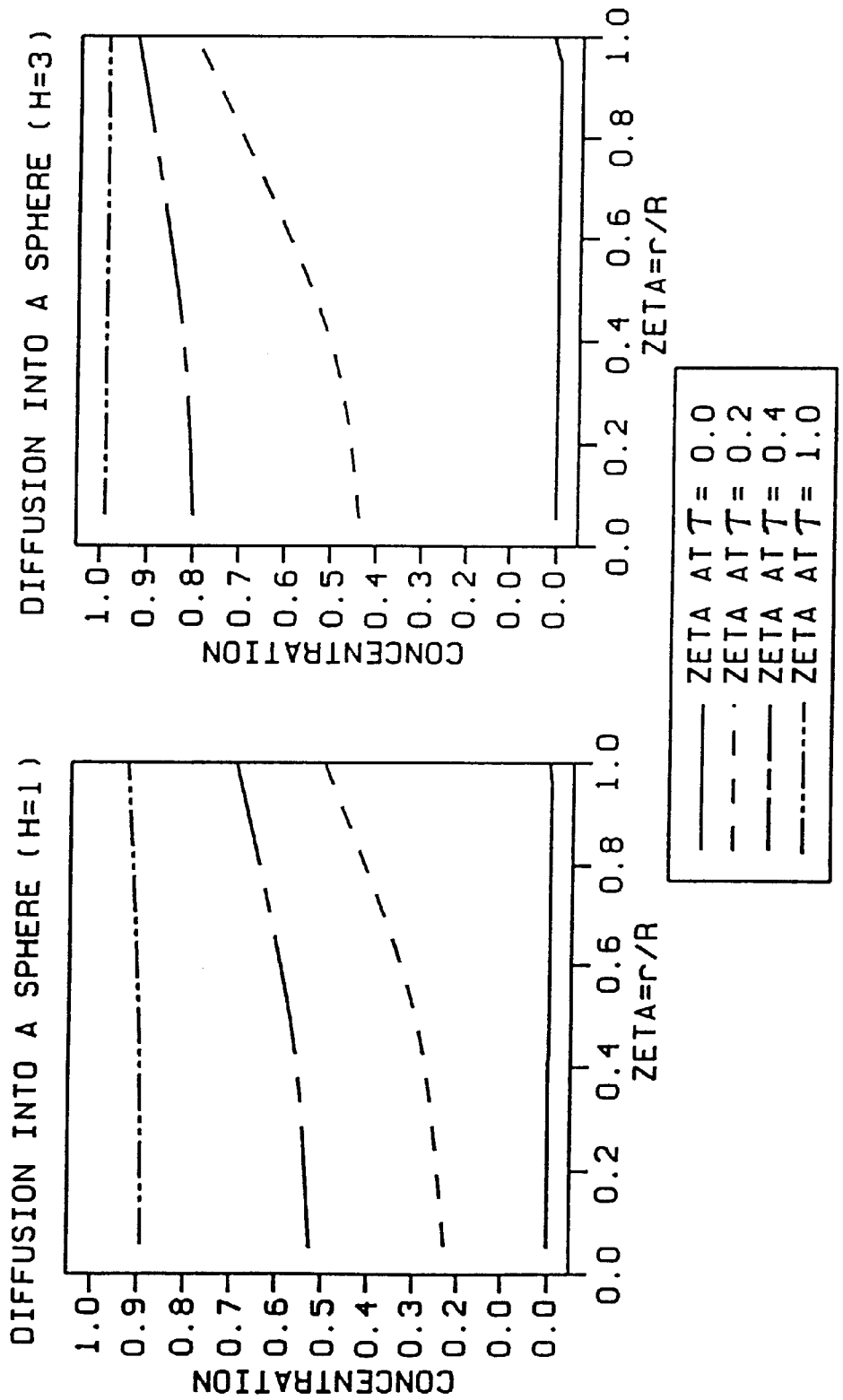
FIG. 4 includes two charts showing the concentration of a boc-amino acid as a function of the distance from the center of the resin bead at four points in time for high film resistance and low film resistance to mass transfer.

The reactor 5 is shown in more detail in FIG. 2. It includes a housing 15 in which a rotatable basket 17 is mounted for rotation. The housing 15 is preferably closed to the atmosphere to prevent evaporation of reactants and washes. A space 18 is defined between the basket 17 and housing 15. The basket 17 is mounted on a shaft 19. The shaft 19 is operatively connected to an appropriately sized motor M to rotate the basket 17, to produce an acceleration of at least 10 gravities (g's) at the surface of the basket. Preferably, the acceleration is greater than 15 g's, and more preferably, the acceleration at the surface of the basket is 50 g's or greater. To achieve an acceleration of 50 g's at the circumference of the basket, a basket with a radius of 15 cm must rotate at a rate of 546 rpm. The acceleration that can be obtained is limited by the mechanical strength of the reactor and the compressibility of the resin.

The basket 17 has a solid bottom 21, a perforated cylindrical wall 23, and a lip 22 extending inwardly from the top of the wall 23. The perforations in the side wall 23 preferably are in the range of 2–5 mm. A filter cloth or mesh liner 25 is provided on the inner surface of the basket wall 23 and is sized to prevent the passage of resin R through the wall 23. The mesh liner 25 preferably has a mesh size approximately one-tenth (0.10) to one third (0.33) of the diameter of the resin particles so that it will retain the beads in the basket, yet let liquid pass through. A slurry input pipe 24 is connected to the three-way valve V1 via the line 8 for introducing a slurry of the solid phase. The pipe 24 preferably has an elbow 26 at its end to direct the slurry against the wall 23 of the basket 17. The centrifugal forces generated from spinning the basket are generally sufficient to form a smooth resin cake on the basket wall. However, the pipe 24 may include mechanical means for spreading the slurry to gain a uniform cake depth on the wall 23. The mechanical spreading means may include, for example, an axially or vertically extending blade which is movable radially in the basket to be set a desired distance from the basket wall 23. A reactant feed pipe 27, connected to the line 11, extends into the basket 17 and includes a plurality of spray nozzles 29 which spray amino acid solution, or wash solvent, evenly over the rotating bed of solids. The return line 13 allows for reactants or washes which have passed through the basket 17 to quickly exit the reactor 7 and return to the receiver/sump 5. In this manner, the reactor 5 will not contain a pool of liquid which will contact or submerge the basket. That is, the level of fluid in the reactor will not rise in the housing 15 to the bottom 21 of the basket 17. Because the reactor shell will not be flooded, there will be no fluid which will create a drag which would require the motor M to work harder.

Instrumentation may be provided for automatically charging the desired quantities of liquids into the make-up tank 3, for monitoring the inventory of liquid in the receiver/sump 5, and for monitoring the flow rate of liquid into the reactor 7. In addition, an optional batch sequencer S may be added to more fully automate the entire operation. Instrumentation (such as an IR detector) may also be provided to track the progress of the deblocking and the washing so that the synthesis can be monitored in real time. In addition, the IR detector can serve as an integral part of an automated process and testing for unreacted free amines can be performed as soon as the IR detector indicates that the reaction has ceased.

A design using non-metallic or highly corrosion resistant wetted surfaces might prove necessary for some products. In such cases, the components of the reactor system 1 can be made of, or lined with, non-reactive materials. Such materials include, for example, high nickel alloys, such as Hastelloy available from Haynes Int'l Inc. of Kokomo, Ind., Teflon®, a polytetrafluoroethylene coating available from E. I. du Pont deNemours, or 316 stainless steel.

A synthesis may be performed as follows. Resin, and a slurry solvent are charged to the make-up tank 3, and the agitator is turned on. The beads used for the resin slurry are small beads, preferably less than 100µ in diameter and which are 0.2%–1.5% cross-linked. For example, the resin may consist of boc-Pro-RCM (a Merrifield resin having a boc-Proline bound thereto, such as is available from Sigma Chemical), and the solvent may be dichloromethane (DCM). The temperature may be adjusted to a predetermined temperature (such as 30° C.) by means of the temperature controller TIC on the tank 3. While the resin slurry is stirring, the basket 17 is started spinning, and adjusted to the desired rotational speed (such as 1000 revolutions per minute) to produce an acceleration of at least 10 g's, and preferably greater than 15 g's, and more preferably, 50 g's or greater. The resin slurry is charged directly to the reactor through line 8 and pipe 24. The basket 17 is free of liquid when the slurry is introduced into the basket. The centrifugal forces acting on the resin will cause the resin to form a relatively even cake R (FIG. 2) on the inside surface of the basket. The cake R is preferably built up to an initial depth of between 2–6 cm. Other depths could of course be used. Additional slurry solvent or recycling of filtrate may be introduced into the make up tank 3 to flush residual resin into the reactor 7. The metering pump P2 is activated to recycle slurry solvent through the reactor to ensure that a uniform cake is formed in the reactor. Once the cake R reaches the desired thickness, any remaining slurry solvent is transferred to waste by diverting 3-way valve V3 to waste and operating the pump P2 until the receiver/sump 5 is empty.

The blade or knife discussed above can facilitate the spreading of the slurry on the side wall to ensure that a bed of even thickness is produced. As the slurry is applied to the wall 23 of the basket, if the slurry builds up to a depth greater than desired, the blade will spread out the extra slurry, as can be appreciated. As noted however, such mechanical spreading means generally are not required to make a smooth resin bed.

A solution to deprotect the N-terminus of the resin-bound peptide is made up in the make-up tank 3. Examples of deprotection solutions include pure trifluoroacetic acid (TFA), or solutions of TFA and DCM (dicloromethane). The deprotection solution is transferred to the receiver/sump 5 through line 6. Pump P2 is activated, and the deprotection solution is cycled through the reactor/sump loop. The solution is pumped into the reactor from the receiverlsump 5 through line 11 and pipe 27. The deprotection solution is directed against the slurry bed by the nozzles 29 and passes through the bed and into the space 18 between the basket 17 and housing 15. The solution exits the reactor 7 and returns to the receiver/sump 5 through line 13. Any residual slurry solvent in the lines and resin bed may be purged by diverting a first portion of the centrate exiting reactor 7 to waste or recovery through valve V4 in line 13. This will prevent slurry solvent from mixing with the deprotection solution in the sump/receiver 5. Following the purge of the slurry solvent, the remaining centrate exiting the reactor 7 is diverted to the receiver/sump 5 for recycling to the reactor 7. Recycling continues for a predetermined amount of time (preferably about 3 minutes). Following the deprotection, the solution is diverted to waste or recovery through valve V3, as described above with respect to the slurry solvent.

If desired, a second deprotection step may be conducted to ensure complete deprotection of the N-terminus of the resin-bound peptide.

The resin may be washed (with, for example, DCM) to remove the deprotection solution. Washing is conducted by charging the required amount of solvent to the make-up tank 3, transferring the solvent to the receiver/sump 5 with pump P1, and activating pump P2. The wash solution is cycled through the reactor 7 and receiver/sump 5 for a determined amount of time, i.e., 3 minutes. As before, the valve V4 is initially set to waste to remove any remaining deprotection solution from the system. The valve V4 is then set to cycle, and the wash is cycled through the system. After the wash is complete, the wash is purged from the system through valve V3.

An additional wash (with isopropanol, for example) may be performed to shrink the resin.

The peptide is then deprotonated by washing the resin with a solution of base, such as diisopropyl ethylamine (DIEA), for about 20 minutes.

An additional DCM wash may be performed to remove the DIEA base.

The resin may be shrunk by washing it with methanol (MeOH) or dimethyl formamide (DMF).

The resin may be swollen by washing it with DCM.

The next amino acid (for example, boc-arginine) to be added to the peptide chain is charged to the make-up tank 3. It is preferably preactivated and the make-up tank 3 is also charged with a suitable solvent or solvents, such as DCM and DMF, at the same time the tank 3 is charged with the amino acid. A coupling agent such as DCC or DIC is then added to the amino acid solution in the make-up tank 3. Following a period of preactivation when the majority of insoluble by-products are formed, the valve V1 is operated to direct the activated amino acid to the receiver/sump 5 through filter F1 to remove insoluble by-products of the activation process. The filter F1 is of a size which will remove substantially all of the insoluble by-products of the activation reaction. The filtered amino acid solution is then recirculated through the reactor, as described above, until the coupling is complete.

Because neither the housing nor the basket is flooded during a reaction, less liquid is needed than would be needed with a stirred tank reactor, a shaken flask reactor, or even a flooded rotating basket reactor. This ability to use less liquid allows for the use of higher concentrations of amino acids without using more amino acids, and thus without increasing the expense of the operation. Thus, the amino acid concentration may be increased, for example, to 300 mmol/liter of solution without increasing the amount of the raw amino acid used. As is known, the reaction rate is a function of the concentration of the reactant. Thus, the ability to use less liquid increases the reaction rate of the coupling step. The temperature of the activated amino acid may be controlled and adjusted in the make up tank 3, and as it recirculates through heat exchanger H1. The endpoint of the coupling reaction may be confirmed by testing samples of the resin withdrawn from the reactor.

The resin may be washed with a solvent such as DMF.

Insoluble by-products may be removed from the resin by washing it with MeOH.

Methanol may be removed from the resin by washing it with a solvent such as DCM.

The process repeats for the next amino acid in the sequence. As can be appreciated, the filter cloth and the perforated side wall of the basket replace the filtering frit which is used in either stirred tank or tubular SPPS reactor systems. The elimination of the geometrical constraints of a small and separate filter frit in the discharge path frees the reactor system from the pressure constraints imposed upon the system by the frit (i.e., the designer need not worry about damaging a frit). The maximum pressure to which the system can be exposed is thus governed by the strength of the resin beads and depth of the resin bed (the pressure cannot be so great as to damage or greatly compress the resin beads) and the strength of the basket 17.

In between each step (i.e. while the receiver/sump 5 is being charged with the next solution) the basket 17 continues to spin. This ensures that most of the prior solution will be quickly removed from the cake R by centrifugal force before the next solution is introduced into the reactor 7. Further, as noted, the valve V4 is opened to "waste" for a short period at the beginning of each cycle. This will further purge the system of any of the prior solution which may not have been forced out of the cake R by the continued rotation of the basket, and which was forced out by the current solution. This will ensure that not more than a minimal amount of the prior solution remains in the system—and facilitates the control of exposure of the peptide chain to the reactants or wash.

As noted, the basket and resin bed are not flooded. Thus, all the reactants and liquids which are introduced into the basket pass through the cake R with good velocity. That is, the passage of the solution through the cake R will not be impeded by liquid in the space 18 between the basket and the reactor housing. Thus, the contact time of the peptide with the reactant or wash can be carefully and closely controlled by continuously rotating the basket and timing the duration of operation of the pump P2.

The relative velocity of fluid to particle is a design variable that can affect system performance, product yield, and quality. When the reactant or wash solution is introduced into the basket 17, the liquid passes through the resin and filter cloth, as noted above, and into the housing 15 to be recirculated back to the receiver/sump. As long as the rate at which the liquid exits the reactor is essentially equal to or exceeds the rate at which liquid is introduced into the reactor, the reactor will not flood. Depending on the space between the bottom of the reactor basket and the bottom of the housing, the liquid supply rate can be slower than the liquid exit rate, as long as the cycle is timed to end before the liquid reaches the level of the basket bottom. The velocity at which the solution can pass through the resin and the filter cloth is a function of the resistance (Kp) of the resin to the passage of liquid therethrough and of the resistance (B) of the filter cloth to the passage of liquid therethrough. $K_p$ and B are calculated according to the following equations:

$$Kp = \frac{-\mu \alpha C_s}{A^2 \Delta P} \text{ and } B = \frac{-\mu R_m}{A \Delta P}, \quad 1$$

where $\mu$=the viscosity of the liquid;

$C_s$=the concentration of solids in the liquid;

A=the area of filtration which equals the area of the filter cloth used in the basket;

$\Delta P$=pressure drop through the resin bed;

$\alpha$=the specific resistance of the cake (resin) to the passage of the solution therethrough (in m/kg) and is a function of porosity; and $R_m$=the resistance of the filter cloth to the flow of the solution therethrough.

The forces acting upon a body in a centrifuge may be described by the following equations. The acceleration $\alpha$ of an object in a centrifuge of radius R rotating at $\omega$ rad/sec may be obtained by the following equation:

$$\alpha = R\omega^2 \quad 2$$

The above equation may be expressed in gravities by dividing the acceleration by the acceleration due to gravity (980 cm/sec$^2$).

The pressure drop across a bed of resin may be obtained in the following manner. The static pressure acting upon a fluid is represented by:

$$dP = \rho g dz \quad 3$$

where P is the pressure, g is the gravitational force, and z is the height of the fluid. Substitution of Equation 2 for the gravitational acceleration in Equation 3 results in:

$$dP = \rho \omega^2 R dR \quad 4$$

Integration between the inner and outer radii of the bed depth results in the following expression:

$$P_i - P_0 = \frac{\rho \omega^2 (R_i^2 - R_0^2)}{2} \quad 5$$

The above equations may be expressed in more convenient terms (revolutions per minute) than in radians per second by the following conversion:

$$\omega[\text{rad/sec}] = \frac{2\pi N[\text{rev/min}]}{60[\text{sec/min}]} \quad 6$$

The pressure drop through the porous media may be represented by the following equation:

$$P_i - P_0 = q\mu \left( \frac{m_c \alpha}{A^2} + \frac{R_m}{A} \right) \quad 7$$

where q is the liquid volumetric flow rate, $\mu$ is the liquid viscosity, $m_c$ is the mass of the cake, $\alpha$ is the specific resistance of the cake to flow, $R_m$ is the resistance of the filter medium to flow, and A is the filtration area. The cake resistance, $\alpha$, may be a function of pressure if the cake compresses. The constants for the cake and media resistances may be obtained by conducting a constant-pressure batch filtration experiment, and plotting the elapsed time divided by the volume of filtrate collected verses the volume of filtrate. The slope of the resulting line is proportional to the cake resistance, and the intercept is proportional to the media resistance.

The basket 17 has an inner radius IR (FIG. 2) equal to the distance from the center of the basket to the radial inner end of the lip 22 and an outer radius OR equal to the distance from the center of the basket to the perforated wall 23 of the basket. In the basket used, the outer radius (IR) was about 15 cm and the lip had a width of about 7.5 cm. The inner radius of the basket used was thus about 7.5 cm. Other size baskets could also be used. As the reactant or wash solution is introduced into the basket 17, solution droplets will merge to form a liquid wall on the inner surface of the resin cake and this liquid wall will be forced through the resin by centrifugal forces. As the flow of solution into the basket increases, the depth of the liquid wall will increase. When the liquid wall is sufficiently deep that the distance to the inner surface of this liquid wall from the center of the basket (R[inner] in Table I pbelow) is less than the inner radius (7.5 cm) of the basket, the solution will overflow the lip 22 of the basket. In this condition, the basket is effectively flooded. As can be seen in Table I below, for a rotational rate of 500 rpm, the basket begins to flood at an inlet flow rate of between 102.8 ml/sec and 115.7 ml/sec for a resin bed depth of 5.5 cm. For a resin bed depth of 2.5 cm, the basket begins to flood when the flow rate is between 217.8 ml/sec and 244.9 ml/sec. For a rotational rate of 1000 rpm, the basket does not begin to flood until the flow rate is much higher. For a bed depth of 5.5 cm, the basket does not begin to flood until the flow rate is between 449.8 ml/sec and 514.1 ml/sec; and for a bed depth of 2.5 cm, the basket does not begin to flood until the flow rate is between 952.5 ml/sec and 1088.6 ml/sec.

The values of Table I below were obtained from a series of filtration calculations using experimentally obtained values of $K_p$ and B which were applied to a centrifuge having a wall area of 63.62 cm². The values of $K_p$ and B were obtained for a constant pressure differential P1 of 11 in. Hg. in the space 18 between the basket and the housing. The filtration parameters thereby obtained were applied to a centrifuge having a 15 cm radius and a basket wall area of 1413 cm² to calculate the liquid flow rates to obtain a pressure drop (in liquid height) for various rotational speeds. A change in the pressure P1 and filtration area will affect the filtration coefficients $K_p$ and B.

TABLE I

CALCULATED FLOW V. PRESSURE DROP ACROSS THE RESIN BED

| Area filter cloth | 63.62 cm^2 | A2/A1 | 22.21 |
|---|---|---|---|
| Area Basket | 1413 cm^2 | P1 (in. Hg) | 11 |
| Kp | 0.00038 s/cm^6 | | |
| B | 0.0051 s/cm^3 | Vol. basket | 8884.00 |
| Vol. filter | 400 ml | Cake ht. | 5.5 (cm) |

| Pressure | P2 (in. Hg) | Flow (ml/s) | Flow (ml/s) | | | | R [inner] cm | |
|---|---|---|---|---|---|---|---|---|
| (cm. DCM) | Bed Depth (cm) | 5.50 | 2.50 | P2/P1 | Kp | B | 1000 RPM | 500 RPM |
| 10.17 | 1 | 12.81 | 27.21 | 0.091 | 8.4738E−06 | 2.53E−03 | 14.84 | 14.36 |
| 20.35 | 2 | 25.70 | 54.43 | 0.182 | 4.2369E−06 | 1.26E−03 | 14.68 | 13.69 |
| 30.52 | 3 | 38.56 | 81.64 | 0.273 | 2.8246E−06 | 8.42E−04 | 14.52 | 12.98 |
| 40.69 | 4 | 51.41 | 108.86 | 0.364 | 2.1185E−06 | 6.31E−04 | 14.36 | 12.24 |
| 50 86 | 5 | 64.26 | 136.07 | 0.455 | 1.6948E−06 | 5.05E−01 | 14.19 | 11.41 |
| 61.04 | 6 | 77.11 | 163.29 | 0.545 | 1.4123E−06 | 4.21E−04 | 14.03 | 10.59 |
| 71.21 | 7 | 89.97 | 190.50 | 0.636 | 1.2105E−06 | 3.61E−04 | 13.86 | 9.66 |
| 81.38 | 8 | 102.82 | 217.72 | 0.727 | 1.0592E−06 | 3.16E−04 | 13.69 | 8.64 |
| 91.56 | 9 | 115.67 | 244.93 | 0.818 | 9.4154E−07 | 2.81E−04 | 13.52 | 7.47 |
| 101.73 | 10 | 128.52 | 272.15 | 0.909 | 8.4738E−07 | 2.53E−04 | 13.34 | 6.08 |
| 111.90 | 11 | 141.37 | 299.36 | 1.000 | 7.7035E−07 | 2.30E−04 | 13.16 | 4.27 |
| 122.08 | 12 | 154.23 | 326.58 | 1.091 | 7.0615E−07 | 2.10E−04 | 12.98 | |
| 132.25 | 13 | 167.08 | 353.79 | 1.182 | 6.5183E−07 | 1.94E−04 | 12.80 | |
| 142.47 | 14 | 179.91 | 381.01 | 1.273 | 6.0527E−07 | 1.80E−04 | 12.62 | |
| 152.59 | 15 | 192.78 | 408.22 | 1.364 | 5.6492E−07 | 1.68E−04 | 12.43 | |
| 162.77 | 16 | 205.64 | 435.44 | 1.455 | 5.2961E−07 | 1.58E−04 | 12.24 | |
| 172.94 | 17 | 218.49 | 462.65 | 1.545 | 4.9846E−07 | 1.49E−04 | 12.05 | |
| 183.11 | 18 | 231.34 | 489.87 | 1.636 | 4.7077E−07 | 1.40E−04 | 11.85 | |
| 193.29 | 19 | 244.19 | 517.08 | 1.727 | 4.4599E−07 | 1.33E−04 | 11.65 | |
| 203.46 | 20 | 257.05 | 544.30 | 1.818 | 4.2369E−07 | 1.26E−04 | 11.44 | |
| 213.63 | 21 | 269.90 | 571.51 | 1.909 | 4.0552E−07 | 1.20E−04 | 11.24 | |
| 223.80 | 22 | 282.75 | 598.73 | 2.000 | 3.8517E−07 | 1.15E−04 | 11.03 | |
| 233.98 | 23 | 295.60 | 625.94 | 2.091 | 3.6843E−07 | 1.10E−04 | 10.81 | |
| 244.15 | 24 | 308.45 | 653.16 | 2.187 | 3.5308E−07 | 1.05E−04 | 10.59 | |
| 254.32 | 25 | 321.31 | 680.37 | 2.273 | 3.3895E−07 | 1.01E−04 | 10.37 | |
| 264.50 | 26 | 334.16 | 707.58 | 2.364 | 3.2592E−07 | 9.71E−05 | 10.14 | |
| 274.67 | 27 | 347.01 | 734.80 | 2.455 | 3.1335E−07 | 9.36E−05 | 9.90 | |
| 284.84 | 28 | 359.86 | 762.01 | 2.545 | 3.0264E−07 | 9.02E−05 | 9.66 | |
| 295.02 | 29 | 372.72 | 789.23 | 2.636 | 2.922E−07 | 8.71E−05 | 9.42 | |
| 305.19 | 30 | 385.57 | 816.44 | 2.727 | 2.8246E−07 | 8.42E−05 | 9.16 | |
| 356.05 | 35 | 449.81 | 952.52 | 3.182 | 2.4211E−07 | 7.22E−05 | 7.78 | |
| 406.92 | 40 | 514.09 | 1088.59 | 3.636 | 2.1185E−07 | 6.31E.05 | 6.08 | |

Figure 5:
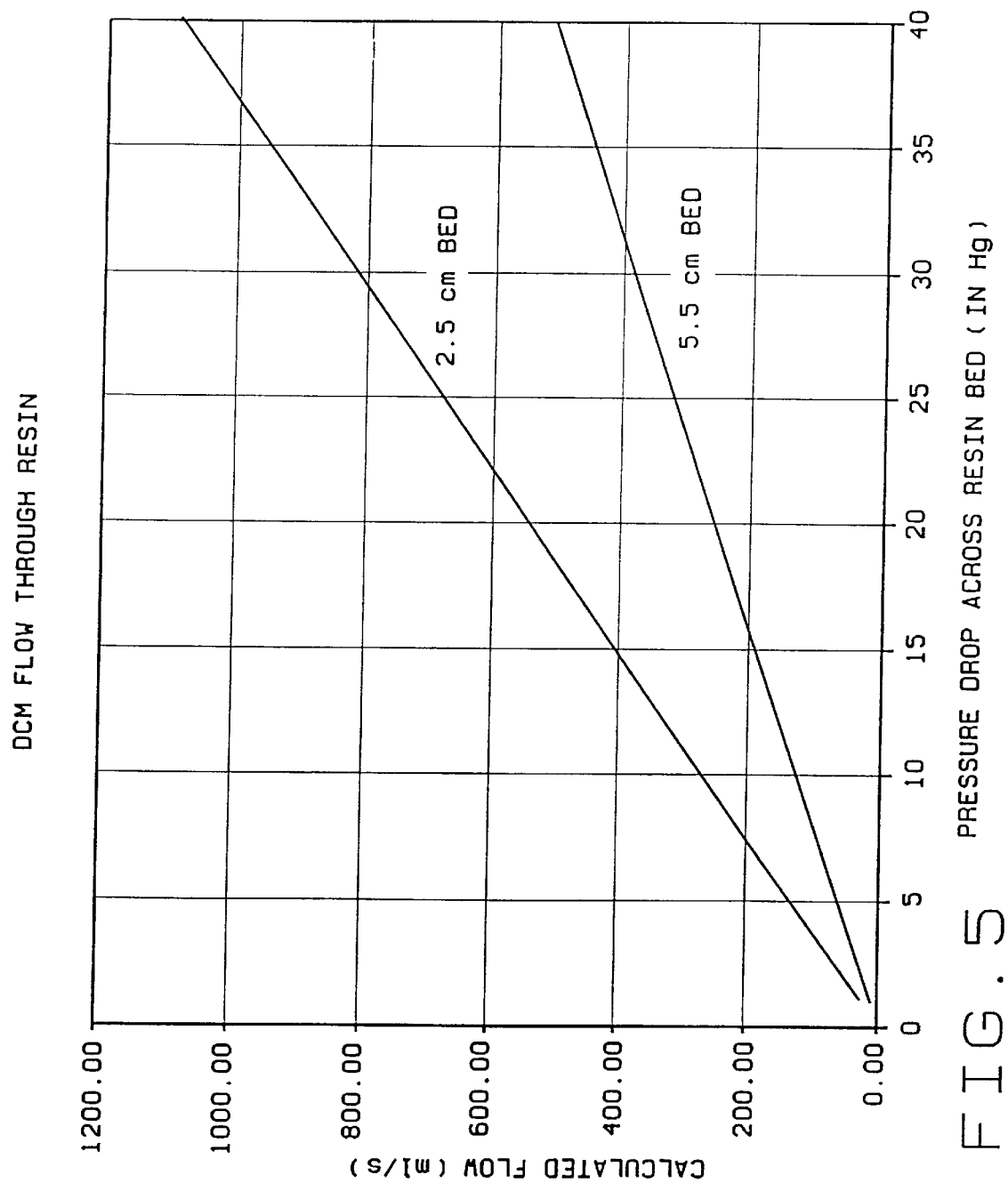
FIG. 5 is a graph charting calculated flow through the resin against pressure drop across the resin bed.

FIG. 5 is a chart which plots the calculated flow rate against the pressure drop across the resin bed in the basket 17.

As can be appreciated, the maximum flow rate before the flooding occurs is a function of the bed depth and the radial width of the lip 22 of the basket. Thus, by increasing the width of lip 22 or by decreasing the bed depth, the maximum possible liquid flow rate can be increased. The operation of the reactor will not be hindered by some surface liquid on the resin bed (provided a substantial amount of liquid does not pass over the lip 22 to by-pass the bed). What is important is that the basket not be submerged (i.e. that there is no liquid filling the space 18 between the basket wall and the housing). This surface liquid could serve to increase the velocity of flow through the resin bed at the cost of slightly greater liquid volume within the rotating basket. The ability to vary the rotational speed at will, and with no limitations set (because the basket is not submerged in liquid) permits higher fluid velocities to be obtained than when a submerged cylinder is rotating in a flooded tank or shell.

The uniform contacting of liquid and solids is essential to the efficient operation of the reactor. Satisfactory contacting of the resin with liquids may be achieved with an evenly dispersed spray of liquid on the resin, a uniform bed depth, and by careful selection of the liquid flow rate and basket rotational speed. The flow rate of liquid through a bed of solids is often directly proportional to the pressure drop across the bead, and inversely proportional to the bed depth. However, the resin is somewhat gelatinous. High centrifugal forces may cause the resin bed to compress, thereby increasing the resistance to the flow through the resin bed. If the bed is compressed at a sufficiently high pressure, the liquid flow through the bed may decrease with increasing pressure drop. There thus may be a finite rotational speed which maximizes the flow of liquid.

Table I, above, shows rotational rates of 500 and 1000 rpm in a basket having a radius of 15 cm, which correspond to centrifugal accelerations (at the inner surface of the basket wall of 41,123 cm/sec$^2$ (41.9 g's) and 164,494 cm/sec$^2$ (167.8 g's), respectively. However, it may be possible to expose the resin beads to much higher rates of acceleration before the compression of the beads by the centrifugal force hinders the flow of fluid through the resin bed. Bead compression is a function the rigidity of the bead, which in turn, is related to the degree of cross-linking of the resin.

EXAMPLES

An IEC centrifuge equipped with a variable-speed motor and a stainless steel basket and a Cole-Palmer Masterflex Model 7518-12 peristaltic pump functioned as the reactor. The basket had an inner diameter of 13 cm and a height of 5 cm. Liquid was added to the centrifuge through a Masterflex Phar-Med hose, type 6485-24, which directed the flow of liquid to the top of the basket hub, which broke up the liquid stream into a series of coarse droplets. This design did not permit complete or full coverage of the resin surface with a uniform spray. The approximate liquid flow was 200 ml/min. Amino acids and HOBt were preactivated with DCC. The insoluble DCU was removed from the activated amino acid solution by vacuum filtration before addition to the reactor. Alcohol (methanol) washes were not required, since the preactivation step removed the vast majority of the DCU. The method was otherwise identical to that set forth in Table II below. The basket rotation was approximately 500 RPM, which corresponds to an acceleration of about 18.2 g's. The (flooded) pressure drop across 1 cm of liquid with a specific gravity of 1.0 under the above condition was 1645 N/m$^2$ (0.24 psi.). The centrifuge filtration area for the reactor is 204 cm$^2$, and the minimum superficial liquid velocity of an empty basket (at a flow rate of 200 ml/min) is 0.98 cm/min. The actual flow velocity across the resin beads is inversely proportional to the cake porosity, and should be 10 to 100 times this estimated flow rate.

Two sets of experiments were performed. The first set was conducted to evaluate the behavior of the resin in the absence of chemical reactions. The resin was dispersed in DCM or DMF, and charged to the centrifuge which was lined with a polypropylene 1–3 micron filter cloth. The resin formed a uniform bed on the cloth, which swelled and shrunk as it was exposed to DCM, DMF, and MeOH. The cake had no tendency to fall during short periods after the centrifuge was stopped. However, the cake did have a tendency to fall if left to dry overnight. Although the cake did crack as it dried, the cracks tended to be quite narrow. Voids did occasionally form, but quickly disappeared during the next solvent wash. The introduction of a liquid to the surface of the resin bead was noted to cause the surface to smooth out. This slight cracking and void formation thus is not believed to have affected the flow of the liquid through the cake, and liquid flow through the cake is believed to have been homogeneous. Resin was also found in the effluent at the beginning of the wash, but the effluent quickly cleared up as it recycled. The liquid recycle worked extremely well, as no net accumulation of solvent occurred within the centrifuge and it allowed fast flow contact to be effected as long as desired. Some solids losses from a centrifuge at the beginning of the feed and wash steps are normal, and were expected in this experiment because no retaining rings were used to hold the cloth against the wall of the basket. The results of the first experiment were highly favorable, and confirmed the mechanical feasibility of the reactor system.

In the second experiment, the dipeptide boc-Arg-Gly was synthesized on a methylbenzhydrylamine (MBHA) resin to demonstrate the feasibility of the reaction apparatus for small peptides. And the final three amino acids of Leuprolide (pGlu-His-Trp) were coupled to fonn Leuprolide to demonstrate the feasibility or the reation apparatus for intermediate length peptides. The method employed is set forth below in Table II.

TABLE II

Solid Phase Synthesis Method

| Step | Operation | Approx. Time |
| --- | --- | --- |
| 1 | 1 × DCM wash (First amino acid only) | 3 min. |
| 2 | 1 × 50% TFA/DCM wash containing 0.5% DTE and 1.0% 2-methylindole after introducing Cys | 3 min* |
| 3 | 1 × 50% TFA/DCM wash containing 0.5% DTE and 1.0% 2-methylindole after introducing Cys | 20 min |
| 4 | 2 × DCM wash | 3 min* |
| 5 | 2 × 5% DIEA/DCM neutralization | 4 min each* |
| 6 | 1 × DCM wash | 3 min* |
| 7 | 2 × MeOH wash (only done for first amino acid) | 3 min each |
| 8 | 2 × DMF wash | 3 min each* |
| 9 | React with preactivated boc-Amino Acid | 30 min. minimum |
| 10 | Ninhydrin Test | |
| 11 | Ninhydrin Test (if necessary) | |
| 12 | 2 × DMF wash | 3 min each* |
| 13 | 2 × DCM wash | 3 min each* |

*Wash time increased to 5 minutes for Leuprolide.

In the first (i.e., boc-Arg-Gly) synthesis, 20 grams of MBHA resin with an incorporation rate of 1 meq of protein/g of resin was used as the starting material. 60 mmol (3 eq) of boc-Gly, HOBt, and DCC were used in the first coupling. The amino acid was preactivated for 15 minutes, and the DCU removed by filtration. After 1 hour reaction time, the centrifuge was stopped, sampled, and tested for free amines by the Ninhydrin test. The sample passed the Ninhydrin test. The batch was deblocked with DCM and TFA and allowed to stand overnight.

The next coupling was conducted with 60 mmol of boc-Arg(TOS) by the same procedure set forth above with the boc-Gly. Samples taken at 1 hour and 2 hours into the coupling reaction failed the Nnhydrin test. The batch was recoupled with 1.5 eq of boc-Arg(TOS), HOt, and DCC preactivated for 3 minutes (to minimize cyclization to Lactam). The Nmhydrin test then passed.

The second part of the experiment included adding the last three amino acids (Glu-His-Trp) in Leuprolide. Pre-Leuprolide (post-Ser) was obtained. The peptide-resin contained about 0.5 meq of peptide/gm of resin at this point. The method used was identical to the method set forth in Table II above, except that a solvent recirculation vessel was added which was composed of a round bottom flask and a sealed ground-glass head with a dip tube. The opening in the top of the centrifuge was covered with a plastic beaker with a slot cut into it to hold the feed hose. These changes were done in order to reduce solvent losses by evaporation.

The first coupling with the new set-up was with boc-Trp. A sample passed the Nmhydrin test after the first hour. The second coupling was with boc-Hs(BOM). The pump speed was increased and the batch was reacted an additional hour. Following the additional reaction time, three samples of resin were taken, one each from the top, middle, and bottom of the cake, and individually tested for free amines. The Ntnhydrin test was very strongly positive for each sample. The batch was recoupled with 1.5 eq of boc-His(BOM), and the batch passed the Nmhydrin test after one hour. The final coupling was with p-Glu. The batch was coupled for one hour, and a sample passed the Nmhydrin test. The final weight of the dried peptide-resin was 32 grams. 2.0 grams of the peptide-resin was cleaved with ethylamine, which yielded 802 mg of protected peptide. The crude peptide was tested by reverse-phase HPLC and showed a typical crude Leuprolide peak.

The results of the first set of experiments indicate that the resin forms a uniform bed on the walls of the centrifuge, and has little tendency to collapse or slump. In addition, the resin bed exhibits minimal cracking. Voids and cracks disappear upon washing, and resin breakthrough is usually quite small. Resin breakthrough of fines in the filtrate was almost non-existent during the coupling experiments, except during the last coupling step. Better methods of sealing the filter media are available and are expected to solve this problem.

As can be appreciated, the reactor system set out above, and the method of its operation keeps the solvents and reactants from flooding the reactor and permits rapid fluid velocities through the resin. The benefits of this system are many, and include:

More precise temperature control during activation, coupling, and deprotection. This is possible because the basket is not submerged in a flooded housing. Thus, all that need be controlled is the temperature of the liquid in line 11 and the input pipe 26.

Reduced use of solvent, since the solvent will not be needed to fill the housing 15 nor to disperse the resin, as is the case in an STR.

Reduced use of amino acid or increased reaction rates. Reaction rates are proportional to the concentration of the reactants. Since the solvent volume may be reduced, the amino acid requirements are also reduced in order to obtain identical concentrations. If the amount of amino acid is not reduced, the concentrations will be higher and the reaction rate will increase accordingly Elimination of highly flammable solvents. Since the amino acids are preactivated and filtered, the DCU levels in the resin should be very small. As a result, the methanol and isopropanol washes are unnecessary. Elimination of alcohol washes will eliminate "squeezing" the resin, which may degrade the resin beads. This will of course also reduce the overall time needed for the coupling of each amino acid to the peptide. As an additional benefit, nucleophilic solvents may be eliminated from the process, which eliminates the risk posed by possible cross-contamination or insufficient removal of these "reactive" species.

Elimination of damage to the resin caused by the shear and grinding action of an agitator to suspend the beads in a stirred vessel. The resin is not stressed by being agitated, as in an STR. There is thus less shear breakage of resin beads from high velocity agitator tip blades.

Ability to remove heat generated by the deprotection reaction. The recirculating liquid may be cooled by an external heat exchanger, and the resin will therefore be continuously exposed to cool DCM/TFA solution.

Ability to improve the quality and yields of the peptide by rapidly removing carbocations generated by the first TFA charge during the deprotection reaction. This may be accomplished since wash liquors may be collected and recycled, or discarded after a single pass through the reactor.

Ability to reduce resin particle size and still maintain high relative velocities of fluid to particle in a stable bed with pressure drops that are manageable by a freely rotating, non-submerged basket.

Improved rates of transfer of reactants between the bulk liquid and the active sites within the resin, since pre-activation of the resin includes removal of DCU by filtration.

Shorter, more controlled fluid contact times, with the non-submerged basket, and faster filtration times which result in shorter time cycles, and a more controlled exposure time of TFA to the peptide-resin.

Elimination of frits which may break or become blocked with resin fragments or insoluble by-products. As noted above, the perforated wall 23 of the basket 17 replaces the frit.

More efficient washing, since the resin may be spun relatively dry between washes, and the first portion of the next wash solvent may be discarded rather than recycled. This has the effect of rapidly purging the resin of the previous solvent.

The accommodation of the shrinking and swelling of the resin bed with the uniform basket cake. Unlike the tubular reactors, the ratio of the volume of the resin bed to the filter area (i.e. the basket wall) is low. The above description is set forth for illustrative purposes only and is not intended to be limiting. Variations within the scope of the attached claims may be apparent to those skilled in the art. For example, DIC may be substituted for the DCC as an activating agent. The use of DIC does not create insoluble by-products (such as DCU) which will clog the resin. The use of DIC as an activating agent thus eliminates the need of the methanol washes and preactivation, which will reduce the overall time required for the synthesis of the peptide. The make-up tank 3 can be removed from the system, and the solutions can all be made up in the receiver/sump tank 5. This would require that the controls associated with the make-up tank be associated with the receiver/sump tank, and for the filter F1 to be placed in line 11 or in a filter loop on line 11. Although the basket is rotated horizontally about a vertical axis, the basket could be rotated about a horizontal axis, such that the basket is on its side, or it could even be rotated about an inclined axis (i.e. at an angle of less than 90° to the vertical). These examples are merely illustrative.

We claim:

1. A method for carrying out solid phase peptide synthesis in a reactor system, the reactor system including a synthesis reactor having a housing, a basket in the housing having a porous wall, the basket being rotatable about an axis, the basket having a smaller diameter than the housing, the basket and housing defining a space between an outer surface of the basket and an inner surface of the housing; the method including spinning the basket at a desired rotational rate; (a) supplying a slurry of resin to the spinning reactor basket to build up a cake of substantially uniform thickness on the wall of the basket; (b) supplying a deprotecting solution to the rotating basket to deprotect the N-terminus of a resin-bound peptide, (c) supplying one or more washing solutions to the rotating basket to wash the deprotecting solution from the cake; (d) supplying an amino acid solution of the next amino acid to be added to the peptide chain and a coupling solution to the rotating basket to add the next amino acid to the peptide chain; repeating steps (c)–(d) until the peptide chain is completed; wherein the deprotecting solution, the washing solution, the amino acid solution, and the coupling agent solution are introduced into the rotating basket at a rate such that the supplied solution will not collect in the reactor housing and submerge the basket, the basket being in an unflooded state during each stage of a peptide synthesis.

2. The method of claim 1 including a step of binding the first amino acid of the desired peptide sequence to an active site of the resin to create the resin-bound peptide.

3. The method of claim 1 including a step of controlling the temperature of said solutions.

4. The method of claim 1 wherein the step of building up said cake, includes building up said cake to a depth of between 2 cm and 6 cm.

5. The method of claim 1 wherein the steps of supplying the solutions to the reactor include spraying the solutions through a nozzle against the resin cake.

6. The method of claim 1 wherein the resin is made of styrene beads.

7. The method of claim 6 wherein said beads have a diameter of less than 100μ and are 0.2%–1.5% cross-linked.

8. The method of claim 1 wherein said spinning the basket includes rotating the basket at a rate fast enough to generate sufficient centrifugal forces to hold the resin cake against the wall of the basket.

9. The method of claim 8 wherein the basket is rotated at a rate sufficient to obtain a centrifugal force at the inner surface of the basket of at least about 10 g's.

10. The method of claim 1 including a step of preactivating the amino acid to be added prior to supplying the amino acid to the reactor.

11. The method of claim 10 including a step of filtering the solution of preactivated amino acid to remove insoluble by-products from the solution before supplying the solution to the reactor.

12. The method of claim 1 wherein the reactor system includes a receiver; the reactor having an outlet in the housing in fluid communication through a first pipe with an inlet to the receiver and the receiver having an outlet in fluid communication through second pipe with an inlet of the reactor, said receiver, said reactor, and said first and second pipes defining a circuit; each of the steps of supplying said solutions to said rotating basket including a step of supplying said solution to said receiver and then transferring said solution to said reactor; said solution being urged through said cake and into said reactor space, said solution flowing back to said receiver through said first pipe.

13. The method of claim 12 wherein each of the steps of supplying said solutions to said rotating basket includes circulating said solutions through said circuit for a determined amount of time.

14. The method of claim 12 wherein the reactor system includes a filter positioned between the reactor and the sump, the method including a step of filtering the solution as it is transported through the circuit.

15. The method of claim 1 including a step of substantially purging a first solution from said reactor system before a second solution is introduced to said reactor.

16. The method of claim 15 wherein said receiver may be placed in communication with a collector, said purging step including a step of transporting any solution in said reactor to said receiver, placing said receiver in communication with said collector, and diverting the contents of said receiver to said collector, said transporting step including spinning said basket at said desired rotational rate so as to purge said first solution before introduction of said second solution has started.

17. The method of claim 16 wherein the first tube may be placed in fluid communication with said collector, said step of purging said first solution from said reactor system further including a step of placing said first tube in communication with the collector for a predetermined amount of time during the step of supplying said second solution to the reactor.

18. A reactor system for carrying out solid phase peptide synthesis, the reactor system including a reactor having a housing including an inlet, an outlet, and a rotatable basket contained withing the housing, the basket having a porous side wall; means for supplying a slurry of resin to said basket so as to build up a cake of substantially uniform thickness on said porous side wall during spinning of said basket; a solution supply tank into which solutions for a peptide synthesis are introduced, the solution supply tank having an inlet and an outlet; the outlet of the reactor being in fluid communication with the inlet of the supply tank over a first line and the outlet of the supply tank being in fluid communication with the inlet of the reactor over a second line; wherein the reactor system is operable to maintain the reactor basket in an unflooded state, such that said solution does not submerge the reactor basket.

19. The reactor system of claim 18 including means for purging the reactor system of a first solution used in the peptide synthesis before a second solution is added to the system.

20. The reactor system of claim 19 including a collector and a first valve in said second line, said first valve being selectively switchable between a first position in which solution exiting said supply tank enters said reactor and a second position in which solution exiting said supply tank is passed to said collector, said purging means including said reactor, sump and valve, wherein said reactor basket is spun after cycling of a solution is completed so that any of said solution in said basket is passed to said solution supply tank, the contents of said solution supply tank then being diverted to said collector through said first valve.

21. The reactor system of claim 20 wherein said purging means further includes a second valve in said first line, said second valve being selectively switchable between a first position in which said reactor outlet is in communication with said supply tank and a second position in which said reactor outlet is in communication with said collector;

wherein said system is operated such that said second valve is switched to its second position for a predetermined period of time during the supplying of said second solution to said reactor.

22. The reactor system of claim 18 including a make-up tank in fluid communication with said reactor and said solution supply tank and a valve operable to selectively direct the contents of said make-up tank to one of said solution supply tank and said reactor.

23. The reactor system of claim 22 wherein amino acids in solution are preactivated in said make-up tank, said amino acids being directed to said solution supply tank through said valve.

24. The reactor system of claim 23 including a filter positioned between said valve and said solution supply tank, said amino acid solution being passed through said filter.

25. The reactor system of claim 22 wherein a resin slurry is produced in said make-up tank, said valve being operated to direct said slurry to said reactor, said reactor including a slurry inlet pipe.

26. The reactor system of claim 25 wherein said slurry inlet pipe directs said slurry against the wall of said reactor basket.

27. The reactor of claim 26 including a spreader to facilitate the formation of a slurry bed on the reactor wall which is of substantially uniform thickness and is substantially smooth.

* * * * *